(12) United States Patent
Webler

(10) Patent No.: US 10,080,872 B2
(45) Date of Patent: Sep. 25, 2018

(54) SYSTEM AND METHOD FOR FFR GUIDEWIRE RECOVERY

(71) Applicant: ABBOTT CARDIOVASCULAR SYSTEMS INC., Santa Clara, CA (US)

(72) Inventor: William E. Webler, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 880 days.

(21) Appl. No.: 14/532,785

(22) Filed: Nov. 4, 2014

(65) Prior Publication Data

US 2016/0120415 A1   May 5, 2016

(51) Int. Cl.
| | |
|---|---|
| *A61B 5/0215* | (2006.01) |
| *A61M 25/01* | (2006.01) |
| *A61M 25/09* | (2006.01) |
| *A61B 5/00* | (2006.01) |
| *A61B 5/026* | (2006.01) |

(52) U.S. Cl.
CPC ......... *A61M 25/09* (2013.01); *A61B 5/02158* (2013.01); *A61B 5/6851* (2013.01); *A61B 5/026* (2013.01)

(58) Field of Classification Search
CPC ... A61B 5/02158; A61B 5/6851; A61B 5/026; A61M 25/0169; A61M 25/09; A61M 25/09041; A61M 2025/0002; A61M 2025/0004

See application file for complete search history.

(56) References Cited

U.S. PATENT DOCUMENTS

| | | |
|---|---|---|
| 788,018 A | 4/1905 | Broyles |
| 931,365 A | 8/1909 | Zimmermann |
| 4,210,029 A | 7/1980 | Porter |
| 4,443,700 A | 4/1984 | Macedo et al. |
| 4,581,530 A | 4/1986 | Brogardh et al. |
| 4,787,396 A | 11/1988 | Pidorenko |
| 5,178,153 A | 1/1993 | Einzig |
| 5,178,159 A | 1/1993 | Christian |
| 5,392,117 A | 2/1995 | Belleville et al. |
| 5,797,856 A | 8/1998 | Frisbie et al. |
| 5,836,885 A | 11/1998 | Schwager |
| 5,860,938 A | 1/1999 | Lafontaine et al. |
| 5,938,624 A | 8/1999 | Akerfeldt et al. |
| 5,964,714 A | 10/1999 | Lafontaine |

(Continued)

*Primary Examiner* — Meredith Weare
(74) *Attorney, Agent, or Firm* — David J. Pitman; Fulwider Patton LLP

(57) ABSTRACT

A kit for coronary treatment comprising a pressure sensing guidewire that includes a pressure sensor for measuring pressure within a patient's vasculature. A sheath comprising a tube having a proximal end and a distal end and defining an internal lumen sized for receiving the pressure sensing guidewire; a hemostasis valve positioned over the proximal end of the tube; a cylindrical element attached to the distal end of the tube, the cylindrical element having an internal lumen sized for receiving a conventional guidewire; wherein the pressure sensing guidewire is configured to be slideably insertable into the tube from the proximal end of the tube; and further wherein, the tube is configured to permit the pressure sensing guidewire, including the pressure sensor, to freely slide distally and proximally within the tube at the election of a user.

1 Claim, 9 Drawing Sheets

(56) References Cited

U.S. PATENT DOCUMENTS

| | | | |
|---|---|---|---|
| 6,033,366 A | 3/2000 | Brockway et al. | |
| 6,089,103 A | 7/2000 | Smith | |
| 6,112,598 A | 9/2000 | Tenerz et al. | |
| 6,142,958 A | 11/2000 | Hammarstrom et al. | |
| 6,167,763 B1 | 1/2001 | Tenerz et al. | |
| 6,193,669 B1 | 2/2001 | Degany et al. | |
| 6,196,980 B1 | 3/2001 | Akerfeldt et al. | |
| 6,248,083 B1 | 6/2001 | Smith et al. | |
| 6,261,246 B1 | 7/2001 | Pantages et al. | |
| 6,296,615 B1 | 10/2001 | Brockway et al. | |
| 6,336,906 B1 | 1/2002 | Hammarstrom et al. | |
| 6,343,514 B1 | 2/2002 | Smith | |
| 6,354,999 B1 | 3/2002 | Dgany et al. | |
| 6,409,677 B1 | 6/2002 | Tulkki | |
| 6,459,921 B1 | 10/2002 | Belef et al. | |
| 6,471,656 B1 | 10/2002 | Shalman et al. | |
| 6,529,760 B2 | 3/2003 | Pantages et al. | |
| 6,558,334 B2 | 5/2003 | Shalman et al. | |
| 6,615,667 B2 | 9/2003 | Smith | |
| 6,659,959 B2 | 12/2003 | Brockway et al. | |
| 6,672,172 B2 | 1/2004 | Tulkki et al. | |
| 6,685,653 B2 | 2/2004 | Ehr et al. | |
| 6,712,767 B2 | 3/2004 | Hossack et al. | |
| 6,738,145 B2 | 5/2004 | Sherrer et al. | |
| 6,796,945 B2 | 9/2004 | Belef et al. | |
| 6,894,787 B2 | 5/2005 | Youngner et al. | |
| 6,901,176 B2 | 5/2005 | Balachandran et al. | |
| 7,000,477 B2 | 2/2006 | Youngner et al. | |
| 7,097,620 B2 | 8/2006 | Corl et al. | |
| 7,173,713 B2 | 2/2007 | Xu et al. | |
| 7,187,453 B2 | 3/2007 | Belleville | |
| 7,259,862 B2 | 8/2007 | Duplain et al. | |
| RE39,863 E | 10/2007 | Smith | |
| 7,347,822 B2 | 3/2008 | Brockway et al. | |
| 7,428,054 B2 | 9/2008 | Yu et al. | |
| 7,447,388 B2 | 11/2008 | Bates et al. | |
| 7,481,774 B2 | 1/2009 | Brockway et al. | |
| 7,492,463 B2 | 2/2009 | Lopushansky et al. | |
| 7,527,594 B2 | 5/2009 | Vardi et al. | |
| 7,532,920 B1 | 5/2009 | Ainsworth et al. | |
| 7,660,492 B2 | 2/2010 | Bates et al. | |
| 7,684,657 B2 | 3/2010 | Donlagic et al. | |
| 7,689,071 B2 | 3/2010 | Belleville et al. | |
| 7,775,988 B2 | 8/2010 | Pijls | |
| 7,832,276 B2 | 11/2010 | Wu et al. | |
| 7,940,400 B2 | 5/2011 | Lopushansky et al. | |
| 8,031,988 B2 | 10/2011 | Arkwright et al. | |
| 8,059,923 B2 | 11/2011 | Bates et al. | |
| 8,151,648 B2 | 4/2012 | Yu et al. | |
| 8,216,151 B2 | 7/2012 | Smith | |
| 8,231,537 B2 | 7/2012 | Ahmed et al. | |
| 8,277,386 B2 | 10/2012 | Ahmed et al. | |
| 8,298,156 B2 | 10/2012 | Manstrom et al. | |
| 8,317,715 B2 | 11/2012 | Belleville et al. | |
| 8,374,689 B2 | 2/2013 | Gopinathan et al. | |
| 8,478,384 B2 | 7/2013 | Schmitt et al. | |
| 8,485,985 B2 | 7/2013 | Manstrom et al. | |
| 8,559,770 B2 | 10/2013 | Donlagic et al. | |
| 8,641,639 B2 | 2/2014 | Manstrom et al. | |
| 8,825,151 B2 | 9/2014 | Gopinathan et al. | |
| 2008/0119739 A1 | 5/2008 | Vardi et al. | |
| 2010/0109104 A1 | 5/2010 | Tiensuu et al. | |
| 2010/0234698 A1* | 9/2010 | Manstrom | A61M 5/007 600/301 |
| 2011/0092955 A1* | 4/2011 | Purdy | A61B 5/0215 604/523 |
| 2011/0137140 A1 | 6/2011 | Tearney et al. | |
| 2011/0178383 A1 | 7/2011 | Kassab | |
| 2011/0178417 A1 | 7/2011 | Kassab | |
| 2011/0190640 A1 | 8/2011 | Bremer et al. | |
| 2011/0245693 A1 | 10/2011 | Hastings et al. | |
| 2011/0264398 A1 | 10/2011 | Niewczas et al. | |
| 2012/0041318 A1 | 2/2012 | Taylor | |
| 2012/0041319 A1 | 2/2012 | Taylor et al. | |
| 2012/0041320 A1 | 2/2012 | Taylor | |
| 2012/0041321 A1 | 2/2012 | Taylor et al. | |
| 2012/0041322 A1 | 2/2012 | Taylor et al. | |
| 2012/0041323 A1 | 2/2012 | Taylor et al. | |
| 2012/0041324 A1 | 2/2012 | Taylor et al. | |
| 2012/0041735 A1 | 2/2012 | Taylor | |
| 2012/0041739 A1 | 2/2012 | Taylor | |
| 2012/0053918 A1 | 3/2012 | Taylor | |
| 2012/0053919 A1 | 3/2012 | Taylor | |
| 2012/0053921 A1 | 3/2012 | Taylor | |
| 2012/0059246 A1 | 3/2012 | Taylor | |
| 2012/0071782 A1 | 3/2012 | Patil et al. | |
| 2012/0072190 A1 | 3/2012 | Sharma et al. | |
| 2012/0101369 A1 | 4/2012 | Patil et al. | |
| 2012/0108943 A1 | 5/2012 | Bates et al. | |
| 2012/0150516 A1 | 6/2012 | Taylor et al. | |
| 2012/0210797 A1 | 8/2012 | Yu et al. | |
| 2012/0220883 A1 | 8/2012 | Manstrom et al. | |
| 2012/0227505 A1 | 9/2012 | Belleville et al. | |
| 2012/0265079 A1 | 10/2012 | Hilmersson | |
| 2012/0271178 A1 | 10/2012 | Smith | |
| 2012/0278008 A1 | 11/2012 | Davies et al. | |
| 2012/0316419 A1 | 12/2012 | Chevalier | |
| 2013/0012824 A1 | 1/2013 | Vanney et al. | |
| 2013/0030300 A1 | 1/2013 | Ahmed et al. | |
| 2013/0030303 A1 | 1/2013 | Ahmed et al. | |
| 2013/0051731 A1 | 2/2013 | Belleville et al. | |
| 2013/0054214 A1 | 2/2013 | Taylor | |
| 2013/0064438 A1 | 3/2013 | Taylor et al. | |
| 2013/0131523 A1 | 5/2013 | Suchecki et al. | |
| 2013/0151163 A1 | 6/2013 | Taylor et al. | |
| 2013/0211728 A1 | 8/2013 | Taylor et al. | |
| 2013/0218032 A1 | 8/2013 | Belleville | |
| 2013/0274618 A1 | 10/2013 | Hou et al. | |
| 2013/0296722 A1 | 11/2013 | Warnking et al. | |
| 2013/0303914 A1 | 11/2013 | Hiltner et al. | |
| 2013/0317372 A1 | 11/2013 | Eberle et al. | |
| 2013/0324864 A1 | 12/2013 | Manstrom et al. | |
| 2013/0331714 A1 | 12/2013 | Manstrom et al. | |
| 2014/0005558 A1 | 1/2014 | Gregorich | |
| 2014/0024235 A1 | 1/2014 | Russell | |
| 2014/0032142 A1 | 1/2014 | Dutta et al. | |
| 2014/0039325 A1 | 2/2014 | Belleville | |
| 2014/0046642 A1 | 2/2014 | Hart et al. | |
| 2014/0058275 A1 | 2/2014 | Gregorich et al. | |
| 2014/0073976 A1 | 3/2014 | Fonte et al. | |
| 2014/0073977 A1 | 3/2014 | Grady et al. | |
| 2014/0081244 A1 | 3/2014 | Voeller et al. | |
| 2014/0107935 A1 | 4/2014 | Taylor | |
| 2014/0142398 A1 | 5/2014 | Patil et al. | |
| 2014/0148693 A1 | 5/2014 | Taylor | |
| 2014/0155770 A1 | 6/2014 | Taylor | |
| 2014/0164969 A1 | 6/2014 | Hart et al. | |
| 2014/0173486 A1 | 6/2014 | Hart et al. | |
| 2014/0187979 A1 | 7/2014 | Burkett | |
| 2014/0207432 A1 | 7/2014 | Taylor | |
| 2014/0222406 A1 | 8/2014 | Taylor | |
| 2014/0236017 A1 | 8/2014 | Degertekin et al. | |
| 2014/0236492 A1 | 8/2014 | Taylor | |
| 2014/0236553 A1 | 8/2014 | Hart et al. | |
| 2014/0241669 A1 | 8/2014 | Belleville et al. | |
| 2014/0243663 A1 | 8/2014 | Taylor | |
| 2014/0247970 A1 | 9/2014 | Taylor | |
| 2014/0248021 A1 | 9/2014 | Belleville et al. | |
| 2014/0249784 A1 | 9/2014 | Sankaran et al. | |
| 2014/0249790 A1 | 9/2014 | Spilker et al. | |
| 2014/0249791 A1 | 9/2014 | Taylor | |
| 2014/0249792 A1 | 9/2014 | Taylor | |
| 2014/0270427 A1 | 9/2014 | Fonte et al. | |
| 2014/0275892 A1 | 9/2014 | Manstrom et al. | |
| 2014/0275945 A1 | 9/2014 | Fonte et al. | |
| 2014/0275946 A1 | 9/2014 | Fonte et al. | |
| 2014/0275947 A1 | 9/2014 | Fonte et al. | |
| 2014/0276109 A1 | 9/2014 | Gregorich | |
| 2014/0276137 A1 | 9/2014 | Burnett et al. | |
| 2014/0276138 A1 | 9/2014 | Millett | |
| 2014/0276223 A1 | 9/2014 | Gustafsson et al. | |
| 2014/0292752 A1 | 10/2014 | Hart et al. | |
| 2014/0303495 A1 | 10/2014 | Fonte et al. | |
| 2014/0303510 A1 | 10/2014 | Fonte et al. | |

(56) References Cited

U.S. PATENT DOCUMENTS

2014/0316289 A1 10/2014 Kassab
2014/0323887 A1 10/2014 Anderson et al.
2015/0133799 A1* 5/2015 O'Connell ........... A61B 5/0215
                 600/486

* cited by examiner

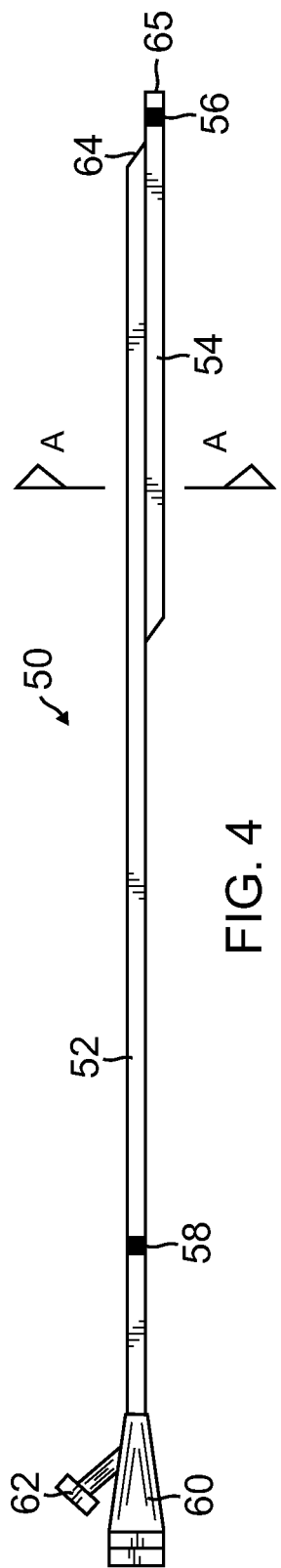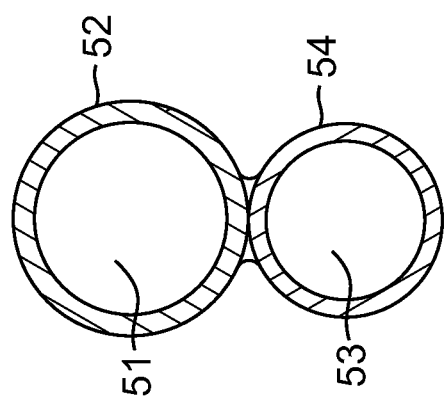
FIG. 4
FIG. 4A

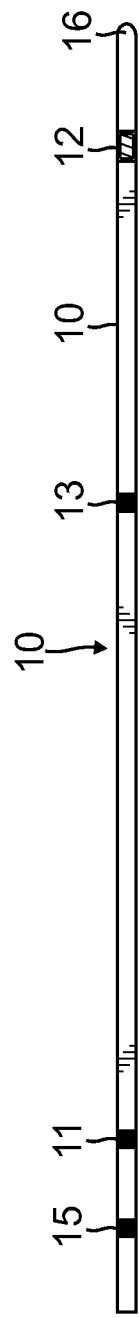
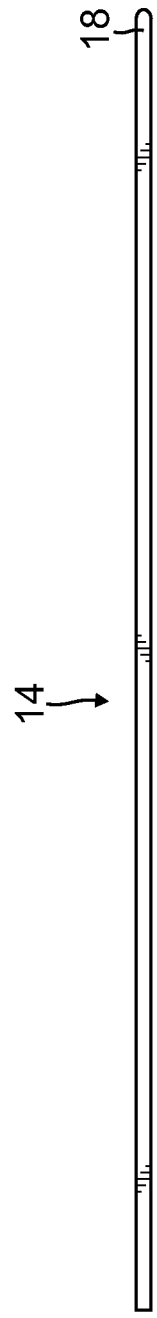
FIG. 5
FIG. 6 (prior art)

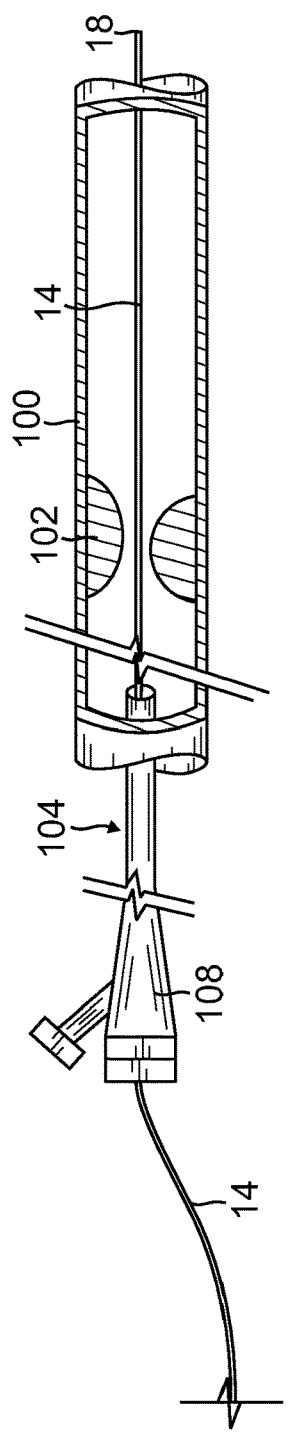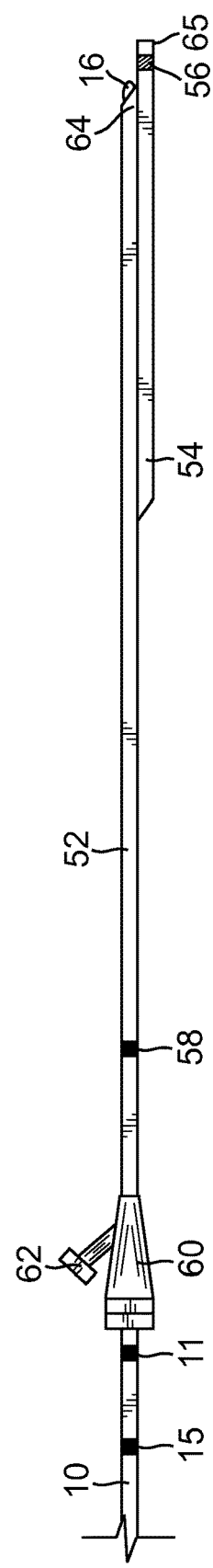
FIG. 7
FIG. 8

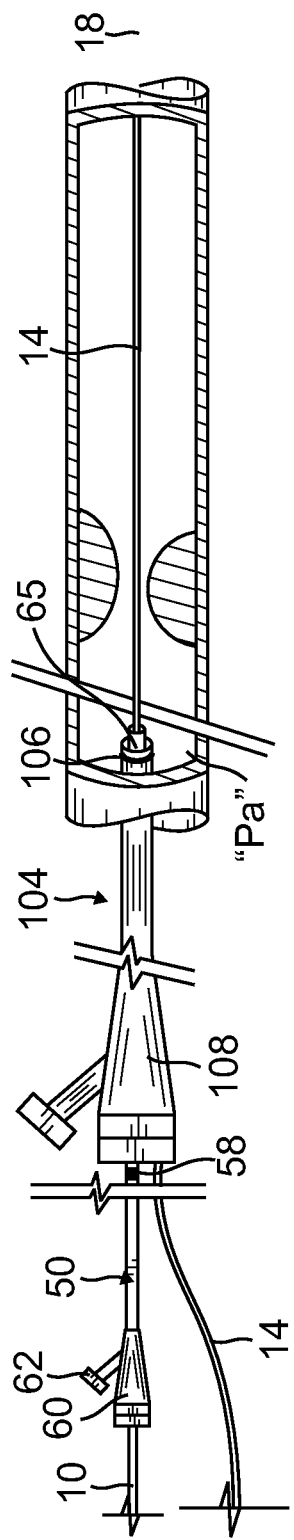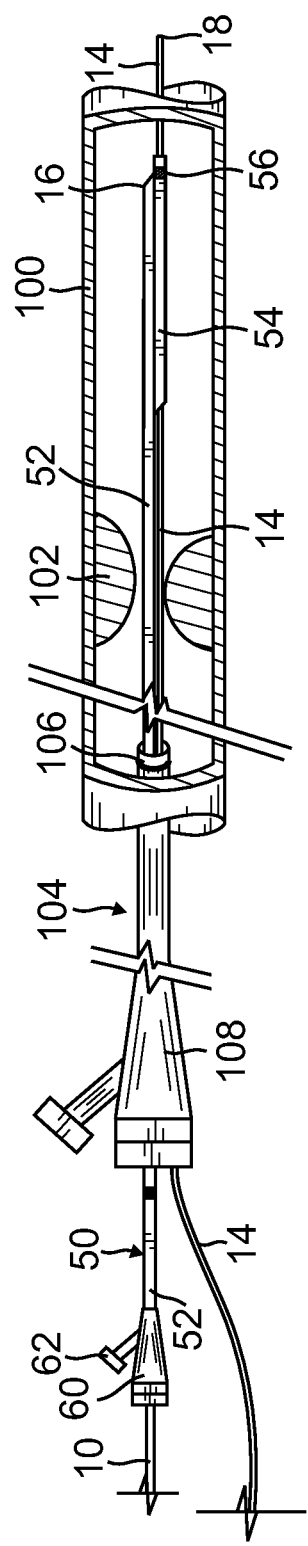

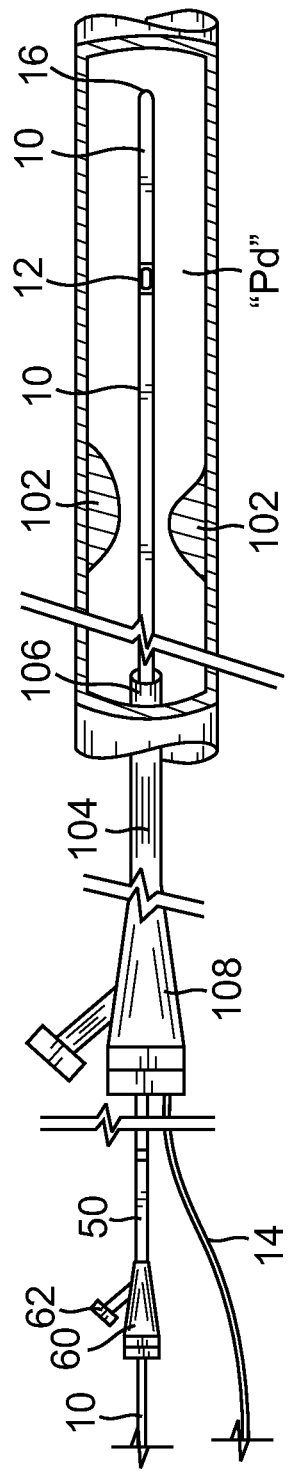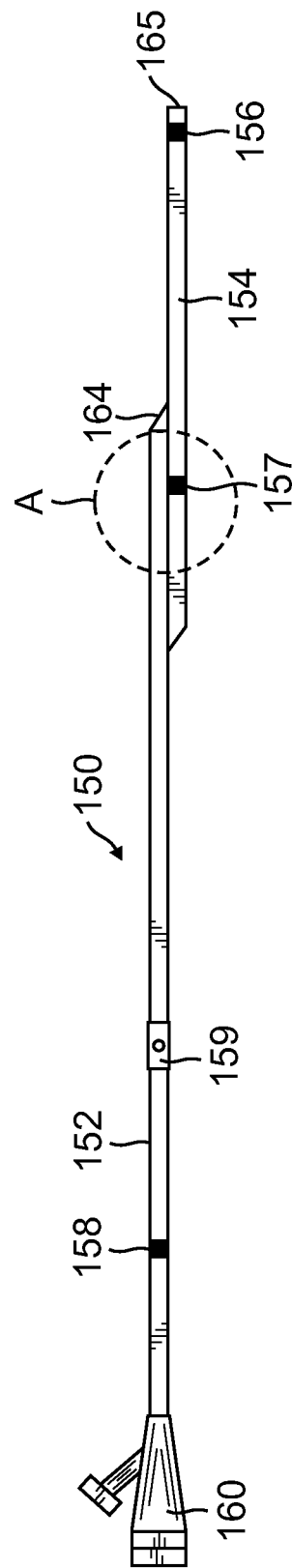
FIG. 11
FIG. 12

SYSTEM AND METHOD FOR FFR GUIDEWIRE RECOVERY

BACKGROUND

The present invention relates to measuring fractional flow reserve ("FFR") in a patient's vasculature. More specifically, the invention relates to a system and method for recovering and re-using a guidewire that is fitted with a sensor configured to measure FFR in a coronary vessel, where an initial attempt to use such an FFR guidewire was made and failed.

Fractional flow reserve is a technique used in coronary catheterization to measure pressure differences across a coronary artery stenosis (that is, a narrowing, usually due to atherosclerosis) to determine to what extent the stenosis impedes oxygen delivery to the heart muscle (myocardial ischemia).

Fractional flow reserve is defined as the pressure behind (distal to) a stenosis or lesion (identified herein as "Pd") relative to the pressure before the stenosis, also known as aortic pressure (identified herein as "Pa"). The fractional flow reserve is obtained by dividing Pd by Pa. The result is an absolute number expressed as a fraction of unity. Thus, for example, an FFR of 0.80 means that a given stenosis causes a 20% drop in blood pressure. If there is no restriction of blood flow by a stenosis, the FFR value is 1.0 (or 100%). Thus, FFR gives some indication of the maximal flow down a vessel in the presence of a stenosis compared to the maximal flow in the hypothetical absence of the stenosis.

As used herein, the terms "FFR guidewire" and "pressure sensing guidewire" are used interchangeably to describe a guidewire that is fitted with a sensor for measuring pressure in order to compute fractional flow reserve.

FFR has certain advantages over other techniques for evaluating narrowed coronary arteries, such as coronary angiography, intravascular ultrasound, or CT coronary angiography. For example, FFR takes into account collateral flow, which can render an anatomical blockage functionally unimportant. Also, standard angiography can underestimate or overestimate narrowing, because it only visualizes contrast inside a vessel.

Other techniques can also provide information which FFR cannot. Intravascular ultrasound, for example, can provide information on plaque vulnerability, whereas FFR measurements are only determined by plaque thickness. Nevertheless, FFR allows real-time estimation of the effects of a narrowed vessel, and allows for simultaneous treatment with balloon dilatation and stenting. On the other hand, FFR is an invasive procedure for which non-invasive (less drastic) alternatives exist, such as cardiac stress testing in which physical exercise or intravenous medication is used to increase the workload and oxygen demand of the heart muscle, and ischemia is detected using ECG changes or nuclear imaging.

Definitions

As used herein, the term "guidewire" contemplates an elongate structure, for insertion into a patient's vasculature, that does not possess a continuous internal lumen configured for receiving a different slideable guidewire. In other words, it is contemplated that a "guidewire" can be independently inserted into the remote regions of a patient's vasculature (even if such a guidewire is initially inserted into the vasculature through the lumen of a guide catheter). Thus, if the guidewire 10' or 10" can be successfully inserted into the patient's vasculature, it may be used for the additional purpose of, for example, guiding the insertion of therapeutic catheters bearing a stent, or balloon, and the like. By corollary, the term "catheter" contemplates an elongate structure, for insertion into a patient's vasculature, that does in fact possess a continuous internal lumen configured for receiving a different guidewire or continuous structure over which the catheter may slide. The term "connected" (and the noun "connection") in respect of a first element connected to a second element is satisfied if movement of the first element necessarily causes similar movement of the second element. The term therefore includes a connection of a first element to a second element via an intermediate element that is connected to both first and second elements.

Known Procedure for Using an FFR Guidewire.

With reference to FIGS. 1-3, during coronary catheterization, a catheter is inserted into the femoral (groin) or radial (wrist) artery using a guide catheter 104 in combination with a specially configured guidewire 10' or 10" in which a small sensor 12 is positioned on the distal end of the guidewire (commonly a transducer) and configured to measure local pressure. Such a guidewire will be referred to herein as an FFR guidewire, alternatively, a pressure sensing guidewire.

Continuing with the known procedure for using an FFR guidewire, the guide catheter 104 is first positioned at an appropriate location within the aorta of the patient. FIG. 3. Thereafter, the FFR guidewire 10' or 10" is advanced through the guide catheter 104, and extended through the vasculature 100 until its distal tip 16, including the sensor 12, is positioned distal to the stenosis 102. The sensor 12 is then used to measure the pressure Pd in the vessel 100 distal to the stenosis 102. This is done during maximal blood flow (hyperemia), which can be induced by injecting products such as adenosine or papaverine into the coronary vessel via the guide catheter 104. In conjunction with this measurement the aortic pressure (Pa) proximal to the stenosis 102 may be measured. This may be accomplished by using a proximal sensor (not shown in the figures) in the guide catheter 104 which is configured to measure pressure at a point immediately distal to the distal end 106 of the guide catheter. A fluid column formed by the blood in the vessel 100 may transmit pressure down a lumen 105 in the guide catheter 104. This allows that the proximal pressure sensor may be positioned in a proximal region of the guide catheter, yet still be able to measure the pressure at a location immediately distal of the guide catheter, for example, at the point marked "Pa" in FIG. 3 via the fluid column in the guide catheter 104. As used herein, a fluid column is defined as a continuous fluid path confined within a tubular structure (in this case the guide catheter's lumen 105) such that the fluid flow resistance of the fluid path, fluid inertial forces and the compliance of the pressure measurement system do not appreciably distort the measurement of the blood pressure just distal to the lumen by a sensor in at the proximal end of the lumen.

The pressure signal of both the distal pressure Pd and aortic pressure Pa is routed to an FFR computing and display system (not shown in the figures). FFR is computed by dividing Pd by Pa and the resultant value is displayed on the system. It may be noted that there are various algorithms for determining Pd and Pa from their pressure waveforms, but there is little significant difference between their physiologic accuracy. There are other types of flow reserve measurements that use these pressure (Pd and Pa) waveforms/ measurements or other sensor modalities. However, pressure-based FFR is the most definitive for determining when a coronary lesion restricts blood flow enough to require lesion treatment such as stenting. An FFR of 0.75 or less is typically taken as the threshold indication that the lesion is hemodynamically significant (will cause ischemia) and the patient will benefit from lesion treatment.

Clinical studies show that, relative to other treatment decision methods, FFR measurement driven treatment decisions lead to both better patient outcomes and less acute and chronic treatment costs. Most significantly, FFR measurement driven stenting has been shown to have much better patient outcomes than medical treatment alone and produces better outcomes than stenting not using FFR. Additionally, it has been shown that if the FFR is 0.80 or greater after coronary treatment, then patient outcomes are improved. In general, the higher the post-treatment FFR value, the better the patient outcome. A low post-treatment FFR may indicate that there is a significant lesion proximal of the treatment site or that the stent ID is too low or not fully deployed. However, a pullback of the FFR guidewire while measuring FFR real-time can identify the source or location of a low post-treatment FFR and guide the user to another treatment site. Thus, FFR measurements show when coronary treatment is justified, if the treatment was successful or incomplete, and can find hemodynamically significant lesions that were not previously recognized or suspected as significant.

The general technology of FFR measurement using an FFR guidewire is well described in the art. A sensor on an FFR guidewire may include electrical, optical, or sonic principles such as described in U.S. Pat. No. 5,178,153, and U.S. Pat. No. 7,689,071 which are incorporated herein in their entirety by reference.

Justification for stent use, demonstration of stent use effectiveness and procedure cost effectiveness are increasingly demanded by hospitals, governments, regulatory bodies and insurance companies. As a result, FFR measurement is gaining popularity and is now used in about 20% or more of coronary cases where treatment is contemplated.

However, one of the problems that has been identified in the art is that an FFR guidewire, such as those exemplified in FIGS. 1-3 and others known in the art, is typically less flexible in some of its distal portions and contains greater changes in flexibility than a conventional guidewire 14 (exemplified in FIG. 6) that is not equipped with a sensor. Surgeons typically use such conventional guidewires when not taking FFR measurements but use it as a simple guiding device for delivering a therapeutic structure such as a stent or angioplasty balloon, or to exchange catheters. This problem is a result of the fact that the structure required to accommodate a sensor 12 inevitably produces a stiff length in the FFR guidewire 10, thus making it less flexible and poorer in negotiating bends in comparison with a conventional guidewire 14. Thus, instances frequently arise in which the FFR guidewire 10 cannot reach a point distal to the target stenosis 102, especially in complex anatomy or lesions, because the path has bends that are too tortuous to be traversed by an FFR guidewire.

Typically, if a surgeon attempts to introduce an FFR guidewire and finds that the stenosis cannot be crossed due to the flexibility profile of the FFR guidewire, the surgeon may have little choice other than to abandon the attempt to measure FFR. He may be obliged to insert a conventional guidewire 14 with a better flexibility profile to reach and pass through the stenosis, and may make the determination on whether to supply a stent or not based on other means such as coronary angiography, intravascular ultrasound, or CT coronary angiography. This failure to pass the stenosis with an FFR guidewire has an unfortunate economic consequence—because an expensive FFR guidewire may be abandoned without it having performed its function, and the more localized pressure information that can be obtained by an FFR guidewire has not been obtained. A further option that a physician may have is to use a catheter that is fitted with a fixed sensor for pressure measurement (referred to herein as an FFR catheter). Here, a conventional guidewire is introduced into the vasculature, and a catheter carrying a fixed sensor is introduced over the guidewire. Such catheters are described in U.S. Pat. No. 8,317,715 and U.S. Pat. No. 8,298,156. However, due to the additional sensor technology, these are expensive items and consequently, if this option is followed, it means that an expensive FFR guidewire and an expensive FFR catheter will have been consumed in the procedure. The original problem persists, in which beneficial use of an expensive FFR guidewire is lost.

Thus, there is a need in the art to address the problems identified here. The present invention addresses these and other needs.

SUMMARY OF THE INVENTION

In one embodiment, the invention is a kit for vascular treatment comprising a pressure sensing guidewire that includes a pressure sensor for measuring pressure within a patient's vasculature. Separately within the kit is a sheath comprising a tube having a proximal end and a distal end and defining a first internal lumen sized for receiving the pressure sensing guidewire. A hemostasis valve attached to the proximal end of the tube is also included in the sheath. A cylindrical element attached to the distal end of the tube is provided, the cylindrical element having a second internal lumen sized for receiving a conventional guidewire. As will be seen, the sheath is configured to be capable of inserting a pressure sensing guidewire distal to a lesion that cannot be reached by the pressure sensing guidewire on its own.

Under this configuration, the tube is sized to slideably receive the pressure sensing guidewire via the hemostasis valve. Further, the sheath is configured so that there is not any connection between the pressure sensing guidewire and the sheath when the pressure sensing guidewire is inserted into the tube (except for temporary clamping action by the hemostasis valve when the hemostasis valve is closed), whereby, when the hemostasis valve is not closed, the pressure sensing guidewire is free to slide distally and proximally within the tube at the election of a physician user, including free to slide completely out of the tube. The absence of any connection between pressure sensing guidewire and sheath (except for the temporary clamping action at the election of a surgeon) has the advantage of allowing the physician user to electively mount the sheath to the pressure sensing guidewire and to slide it proximally and/or distally within the sheath during the procedures described herein. This novel and useful structural feature overcomes the problem in the prior art identified above, in that it allows a physician to follow the procedure described herein to recover the beneficial use of a pressure sensing guidewire which has encountered an unreachable lesion and which would otherwise have lost its beneficial use.

In some embodiments of the kit, the lumen of the tube is open at the distal end, and the lumen of the tube adjacent the distal end is sized to provide a continuous fluid column from a point which is exterior of the distal end of the tube to the pressure sensor inside the tube when the pressure sensing guidewire fills the lumen of the tube.

In some embodiments, the lumen of the tube is closed at the distal end, and the tube includes an opening in a sidewall of the tube, the opening sized for measuring pressure outside the tube when the pressure sensor is located inside the tube. Under this configuration, the pressure sensing guidewire may include a marker located so that when the pressure sensing guidewire is inserted into the tube, the marker is in registration with the hemostasis valve at the same time as the pressure sensor is in registration with the opening in the sidewall.

In some embodiments, the lumen of the tube may be closed at the distal end, and the sheath defines a port that places the lumen of the cylindrical element in fluid communication with the lumen of the tube, the port being configured to provide a fluid column for measuring pressure inside the lumen of the cylindrical portion when the pressure sensor is located inside the lumen of the tube.

In other embodiments, the pressure sensing guidewire may include a marker located so that when the pressure sensing guidewire is inserted into the tube, the marker is in registration with the hemostasis valve at the same time as a distal end of the pressure sensing guidewire is in registration with the distal end of the tube.

In yet another embodiment, the invention is a sheath for recovering the beneficial use of a pressure sensing guidewire that includes a pressure sensor for measuring pressure within a patient's vasculature. The sheath comprises a tube having a proximal end and a distal end and defining a first internal lumen sized for receiving the pressure sensing guidewire. A hemostasis valve is attached to the proximal end of the tube. A cylindrical element is attached to the distal end of the tube, the cylindrical element having a second internal lumen sized for receiving a conventional guidewire. Under this configuration, the tube is sized to slideably receive the pressure sensing guidewire via the hemostasis valve. Further, the sheath is configured so that no connection is formed between the sheath and a pressure sensing guidewire inserted into the tube (except for electively temporary clamping action by the hemostasis valve when the hemostasis valve is closed), whereby, when the hemostasis valve is not closed, a pressure sensing guidewire in the tube is free to slide distally and, alternately, proximally at an election of a user, including free to slide completely out of the tube.

In some embodiments, the lumen of the tube is open at the distal end, and the lumen of the tube adjacent the distal end is sized to provide a continuous fluid column from a point which is exterior of the distal end of the tube to the pressure sensor inside the tube when the pressure sensing guidewire fills the lumen of the tube.

In other embodiments, the lumen of the tube is closed at the distal end, and further wherein the tube includes an opening in a sidewall of the tube, the opening sized for measuring pressure outside the tube when the pressure sensing guidewire is located inside the tube.

In some embodiments, the lumen of the tube is closed at the distal end, and the sheath defines a port that places the lumen of the cylindrical element is in fluid communication with the lumen of the tube, the port being configured to provide a fluid column for measuring pressure inside the lumen of the cylindrical portion when the pressure sensor is located inside the lumen of the tube.

In another embodiment, the invention is a method for assessing a lesion in a patient's vasculature. The method comprises inserting a pressure sensing guidewire including a pressure sensor into a proximal end of a tube via a hemostasis valve attached to the tube. It is ensured that no operable connection is formed between the pressure sensing guidewire and the tube, other than for a temporary clamping action around the pressure sensing guidewire by the hemostasis valve (used to prevent or limit blood leakage). The absence of any connection between pressure sensing guidewire and sheath (except for the temporary clamping action at the election of a surgeon) has a novel and useful advantage, which is described above.

A conventional guidewire having a proximal end and a distal end is inserted into the vasculature of the patient until the distal end of the conventional guidewire is located at a desired location in relation to the lesion. The proximal end of the conventional guidewire is inserted into a distal end of a lumen of a cylindrical element that is attached to the tube. The cylindrical element is advanced distally over the conventional guidewire, along with the pressure sensing guidewire inside the tube, through the patient's vasculature until the pressure sensor reaches a desired location with respect to the lesion. The pressure in the vasculature is measured using the pressure sensor.

In some embodiments, measuring the pressure in the vasculature includes withdrawing the sheath proximally in relation to the pressure sensing guidewire, so that the pressure sensor is located distal of the sheath when the pressure is measured. In further embodiments, measuring the pressure in the vasculature includes withdrawing the conventional guidewire proximally so that the distal end of the conventional guidewire is located proximal of the pressure sensor when the pressure is measured. In yet further embodiments, the tube includes an opening in a sidewall of the tube, and measuring the pressure in the vessel includes bringing the pressure sensor into registration with the opening, whereafter the pressure is measured. In still further embodiments, the sheath defines a port that places the lumen of the cylindrical element and the lumen of the tube in fluid communication, and wherein measuring the pressure includes bringing the pressure sensor into registration with the port, whereafter the pressure is measured.

In another embodiment, the invention is a method for assessing a lesion in a patient's vasculature. The method comprises inserting into the vasculature of the patient a pressure sensing guidewire that includes a pressure sensor. Thereafter, the pressure sensing guidewire is withdrawn from the patient's vasculature. Such withdrawal of the pressure sensing guidewire after it is inserted may be occasioned by the fact that the pressure sensing guidewire cannot cross a lesion in the patient's vasculature, causing the surgeon to withdraw it. The following steps are adhered to in order to recover the beneficial use of the pressure sensing guidewire. In order to accomplish this objective, the pressure sensing guidewire is inserted into a proximal end of a tube via a hemostasis valve attached to the tube. A conventional guidewire having a proximal end and a distal end is inserted into the vasculature of the patient until the distal end of the conventional guidewire is located at a desired location in relation to the lesion. Then, the proximal end of the conventional guidewire is inserted into a distal end of a lumen of a cylindrical element that is attached to the tube. This cylindrical element is sometimes referred to as an Rx portion. Then, the cylindrical element is advanced distally over the conventional guidewire, along with the pressure sensing guidewire inside the tube, through the patient's vasculature until the pressure sensor reaches a desired location with respect to the lesion. At this point, pressure in the vasculature is measured using the pressure sensor.

These and other advantages will appear when the detailed description of embodiments is read in conjunction with the figures.

BRIEF DESCRIPTION OF THE DRAWINGS

FIG. 4 is a side view of a sheath having features one embodiment of the invention.

FIG. 4A is a sectional view of the sheath in FIG. 4, taken substantially along the line A-A in FIG. 4.

FIG. 5 is a side view of a pressure sensing guidewire of a kind known in the art such as shown in FIGS. 1 and 2. However, markers are included on the guidewire in novel locations to facilitate the invention.

FIG. 6 is a side view of a conventional guidewire of a kind that is known in the art.

FIG. 7 is a schematic view in partial cutaway of a vessel that is being assessed according to a first embodiment of the invention, and also showing the state of medical components at a certain stage of one of the steps used in an inventive method.

FIG. 8 is a side view of a sheath having features of the invention, into which a pressure sensing guidewire has been inserted, in the process of carrying out a step of the invention.

FIG. 9 is a schematic view in partial cutaway of the vessel seen in FIG. 7, showing the state of medical components at a subsequent stage of one of the steps used in the inventive method.

FIG. 10 is a schematic view in partial cutaway of the vessel seen in FIG. 7, showing the state of medical components at a subsequent stage of one of the steps used in the inventive method.

FIG. 11 is a schematic view in partial cutaway of the vessel seen in FIG. 7, showing the state of medical components at a subsequent stage of one of the steps used in the inventive method.

FIG. 12 is a side view of a second embodiment of a sheath having features of the invention.

DETAILED DESCRIPTION OF THE SOME EMBODIMENTS

Figure 1:
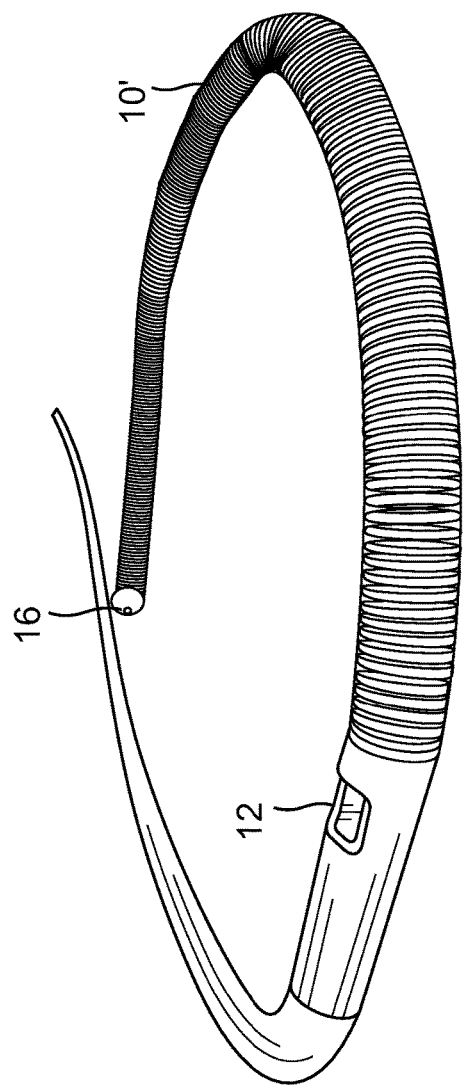
FIG. 1 is a perspective view of a first embodiment of a pressure sensing guidewire of a kind that is known in the art.
Figure 2:
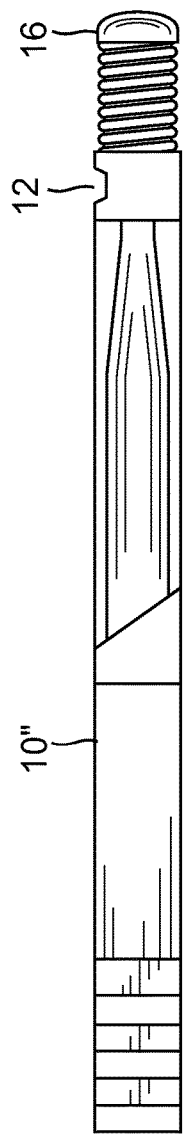
FIG. 2 is a side view in partial cutaway, of a second embodiment of a pressure sensing guidewire of a kind that is known in the art.
Figure 3:
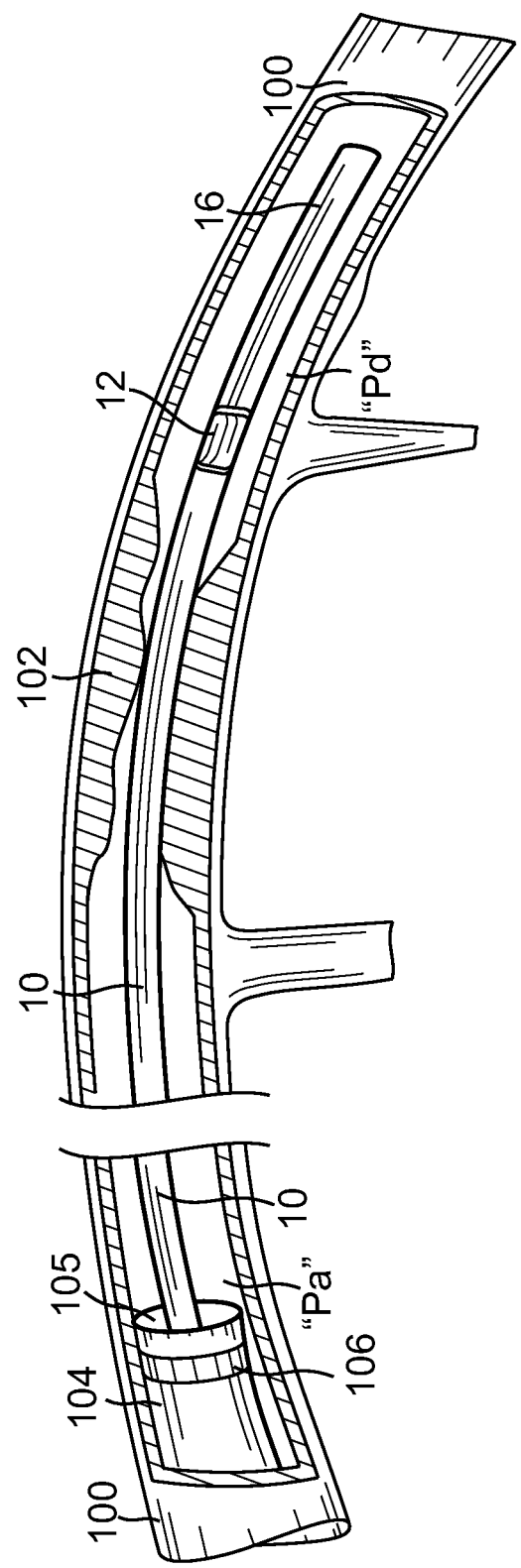
FIG. 3 is side view in partial cutaway of a vessel that is being assessed using a pressure sensing guidewire of the kind that is exemplified in FIGS. 1 and 2.

In some embodiments, the invention includes a novel design for a sheath 50 for recovering beneficial use of an FFR guidewire where a physician has attempted to insert the FFR guidewire beyond a vascular stenosis, but has failed due to a lack of flexibility that typically is associated with FFR guidewires as compared with the higher flexibility found in conventional guidewires.

Turning first to one embodiment of the invention. FIG. 4 exemplifies a sheath 50 that is designed to be extremely simple, comprising few elements and thus being inexpensive to manufacture. The sheath 50 comprises a hollow tube 52 extending the length of the sheath, the tube having an internal lumen 51 (FIG. 4) sized just large enough to freely receive an FFR guidewire of the kind discussed above, and is configured to ensure that no connection is formed between the FFR guidewire and the tube when the FFR guidewire is received within the tube. Preferably, the lumen of the tube has an inner diameter between 0.38 and 0.46 mm, and the outer diameter of the tube is between 0.46 and 0.72 mm. In some embodiments, the wall thickness of the tube may be so thin that the tube itself does not have independent column strength to be pushable; however, as will be seen, the tube is configured to receive an FFR guidewire 10, which will impart an overall stiffness to provide sufficient column strength for pushability. The tube 52 includes a proximal marker 58 adjacent a proximal end of the sheath. The sheath also has a distal marker 56 adjacent a distal end of the sheath. The position of the markers has a functional significance which will be made clear below. In this embodiment, the tube 52 has an open end at its distal end 64. The sheath 50 also comprises a standard hemostasis valve 60 attached to a proximal end of the tube 52, the hemostasis valve optionally including a standard side arm 62. The tube 52 is of course open at its proximal end into the valve. As will appear more fully herein, the valve is configured to form a temporary clamping action over the FFR guidewire at the election of a physician user. It has been noted above that no connection is formed between the FFR guidewire and the tube. It will be understood that, other than the temporary clamping action provided by the valve when the valve is closed, no connection is formed between the FFR guidewire and indeed between any portion of the sheath, thereby providing the advantage described more fully above, in which a physician is enabled to recover the beneficial use of the FFR guidewire should it transpire that the FFR guidewire cannot cross a target lesion in the vasculature of a patient.

The sheath also comprises an "Rx portion" 54 which is a cylinder of relatively short length, (also referred to herein as a cylindrical portion or cylindrical section or element) connected to the tube 52 at the distal end of the tube. The Rx portion 54 defines a lumen 53 which is sized just large enough to receive a conventional guidewire 14 of the kind discussed above. Preferably, the lumen of the Rx portion is between 0.38 and 0.46 mm in diameter, and the length of the Rx portion is between 50 and 400 mm. In preferred embodiments, both the sheath and the tube may be made from extrudable plastics such as polyethylenes, nylons, polyesters, etc. and their blends.

Turning to another embodiment of the invention, a method is described for using a sheath generally of the kind described above in order to redeploy an FFR guidewire that has been found to not be able to reach and pass thorough a vascular stenosis, and which has consequently been withdrawn from the patient's vasculature. This method executes steps that include the following and may be envisaged with reference to FIGS. 7-11.

The Guide Catheter is Left in the Vasculature; Conventional Guidewire Inserted: FIG. 7

The guide catheter 104 which the surgeon would have used in the unsuccessful attempt to place the FFR guidewire is left within the patient's vasculature. A conventional guidewire 14 is fed via the hemostasis valve 108 through the guide catheter 104 and is threaded through the vasculature to position its distal tip 18 at a location distal to the target stenosis 102. FIG. 7. It will be appreciated that the conventional guidewire 14 has a better flexibility profile than the FFR guidewire, so that it may reach and pass through the stenosis 102 that the tortuous anatomy will not allow an FFR guidewire to reach.

The FFR Guidewire is Inserted into the Sheath: FIG. 8

The FFR guidewire 10 (FIG. 5), having been withdrawn from the patient's vasculature, is wetted and flushed.

The sheath 50 is wetted and flushed. Where a side arm 62 is present, the side arm may be used to initially flush the lumen 51 of the tube 52. Where no side arm is present, the lumen of the tube 52 may be flushed by attaching a syringe to the proximal end of the hemostasis valve. The side arm is an optional feature because the guidewire introducer can be easily designed to attach to a syringe and thus, also be used to initially flush this internal lumen of the sheath via the hemostasis valve.

A lubricious coating may be applied to the outer surface and inner surface of the sheath 50, and to the outer surface of the FFR guidewire 10. The FFR guidewire 10 is zeroed in a conventional manner.

The hemostasis valve 60 on the proximal end of the sheath 50 is opened, and the distal end 16 of FFR guidewire 10 is inserted through the valve into the tube 52 until the distal tip 16 of the FFR catheter reaches the distal marker 56 where the proximal end of the FFR guidewire remains only just protruding from the proximal end of the hemostasis valve 60. See FIG. 8. The position of distal marker 11 on the FFR guidewire 10 is located such that when the marker 11 is aligned or registered with the hemostasis valve, the distal end 16 of the FFR guidewire 10 will not extend significantly from the distal opening 64 of the tube 52, but will be as close to the end of the tube's lumen 51 as practical. FIG. 8. Any significant extension of the distal tip 16 of the FFR guidewire 10 from the tube 52 may result in damage being caused to the distal end of the FFR guidewire during positioning of the sheath 50. By positioning the FFR guidewire thus, the tube 52 derives optimal support along its entire length from the FFR guidewire 10 to enhance overall column strength and pushability of the sheath 50 (in combination with the guidewire), while at the same time allowing the outside diameter of the sheath 50 to be minimized. Minimizing the outside diameter of the sheath 50 is beneficial because (a) it allows a smaller outside diameter guide catheter 104 to be used (fewer procedure complications), and (b) allows easier penetration of the stenosis 102 by the sheath 50, as will be described below.

The hemostasis valve is then closed in order to hold the FFR guidewire 10 in place inside the lumen 51 of the tube 52 and to prevent unnecessary blood leakage. FIG. 8.

The Sheath and FFR Guidewire are Inserted to the End of the Guide Catheter: FIG. 9

Then, the proximal end of the conventional guidewire 14 is engaged with the distal end 65 of the RX portion 54 of the sheath 50 by passing the guidewire 14 through the lumen 53 of the RX portion. The hemostasis valve 108 on the proximal end of the guide catheter 104 is opened. The sheath 50, containing the distal portion of the FFR guidewire 10 within the lumen 51 of the tube 52, is advanced through the guide catheter 104 via valve 108 while sliding over the conventional guidewire 14, whereby the RX portion 54 acts as the connection between sheath 52 and guidewire 14. In some embodiments, the proximal marker 58 on the sheath 50 is positioned to alert the physician that, just at the point that the proximal marker 58 reaches the point of entry into the valve 108 of guide catheter 104, the distal tip 65 of the sheath will be positioned near the distal tip 106 of the guide catheter 104, but not outside of the guide catheter. (See FIG. 9.) In other embodiments, the proximal marker 58 may be omitted from the design of the sheath 50 and the insertion of the sheath into the guide catheter 104 may be observed under fluoroscopy. In the latter case, the physician may advance the sheath 50 into the guide catheter 104 until he observes the sheath's radiopaque distal tip marker 56 comes near to the distal tip marker 106 of the guide catheter.

At this point, the hemostasis valve 108 on the proximal end of the guide catheter 104 is closed, to hold and seal the sheath 50 and conventional guidewire 14 in position inside the guide catheter 104 with the distal tip 65 of the sheath being adjacent the distal tip 106 of the guide catheter 104. FIG. 9.

The hemostasis valve 60 on the proximal end of the sheath 50 is then opened. If it has not already been done, the FFR guidewire 10 is advanced up to the proximal marker 11 on the FFR guidewire. (This will indicate that the FFR guidewire is about to exit from the distal end 64 of the tube 52). Then, the hemostasis valve 60 on the sheath 50 is closed to hold and seal the FFR guidewire 10 in place inside the sheath 50. In some embodiments, a second proximal marker 15 on the FFR guidewire 10 is positioned such that the pressure sensor 12 on the FFR guidewire may be positioned distal to the distal opening 65 of the tube 52 of the sheath 50. Thus, the pressure sensor 12 of the FFR guidewire is subjected to and may measure the aortic blood pressure Pa. In some embodiments, the diameter of the lumen 51 in tube 52 in the vicinity of the distal opening 64 of the tube 52 is increased (or is large enough) to allow the aortic blood pressure to be measured without advancing the FFR guidewire's pressure sensor out of the tube's 52 lumen 51.

In yet another embodiment, this marker may be omitted and the FFR guidewire's pressure sensor may be advanced to be adjacent or distal to the sheath's distal tip (radiopaque) marker 56 under fluoroscopy or advanced a prescribed distance.

The FFR guidewire's pressure measurement waveform is then matched to the aortic pressure (Pa) in a conventional manner. Thereafter, the hemostasis valve is opened and if the guidewire has been extended distally out of the tube 52, the FRR guidewire 10 is withdrawn back into the lumen 51 of the tube 52, and the hemostasis valve 60 is closed over the FFR guidewire 10 to hold and seal it in position.

The Sheath Carrying the FFR Guidewire Advanced to Beyond the Stenosis: FIG. 10

Next, and with reference to FIG. 10, the hemostasis valve 108 on the proximal end of the guide catheter 104 is opened and, under fluoroscopy, the sheath 50 is advanced over the conventional guidewire 14 until the radiopaque distal tip marker 56 of the sheath is distal to the target lesion 102.

Then, the hemostasis valve 60 on the proximal end of the sheath 50 is opened and the FFR guidewire 10 is advanced up to its proximal marker 11 or to marker 15 (or by another method, as required, as previously described) position to ensure the pressure sensor 12 is distal to the target lesion or stenosis 102.

The Sheath and the Conventional Guidewire are Withdrawn: FIG. 11

Under fluoroscopy, holding both the conventional guidewire 14 and FFR guidewire 10 stationary relative to the guide catheter 104, the sheath 50 is withdrawn until its distal tip marker 56 is well proximal of the target lesion 102 (until the sheath 50 is not significantly obstructing coronary blood flow). This leaves both the FFR guidewire 10 and conventional guidewire 14 distal to the lesion.

The hemostasis valve 60 on the sheath is closed to seal/hold the FFR guidewire 10 in position distal to the target lesion.

The hemostasis valve 108 is opened and, under fluoroscopy, the conventional guidewire 14 is withdrawn until its distal tip is just inside the RX portion 54 of the sheath (at or near the sheath's distal tip marker 56) and the hemostasis valve 108 on the proximal end of the guide catheter 104 is closed to hold and seal the positions of the sheath 50 and the conventional guidewire 14. This leaves only the FFR guidewire 10 distal to the target lesion 102. FIG. 11. This step is undertaken to minimize the effect that the guidewire and sheath may have on the distal pressure measurement (Pd).

In the conventional manner, adenosine is injected into the guide catheter 104 and the FFR measurement(s) of Pd are made.

Conventional Guidewire Advanced, Sheath and FFR Guidewire are Removed: FIG. 7

Next, both hemostasis valves 108, 60 are opened and, under fluoroscopy, both the sheath 50 and the conventional guidewire 14 are advanced while holding the FFR guidewire 10 in position relative to the guide catheter 104, until the distal tip marker 56 of the sheath 50 is distal to the target lesion. The hemostasis valve 60 on the proximal end of the sheath 50 is closed to hold and seal around the FFR guidewire 10.

Leaving valve 108 open, and holding the conventional guidewire 14 in position relative to the guide catheter 104, the sheath 50 and the FFR guidewire 10 within it are withdrawn over the conventional guidewire 14 and removed. The hemostasis valve 108 on the proximal end of the guide catheter 104 is closed to hold and seal around the conventional guidewire 14. This leaves only the conventional guidewire 14 distal to the target lesion 102 and ready for use by a therapeutic catheter. Thus, the configuration of elements has returned to that depicted in FIG. 7. The sheath 50 (and the FFR guidewire 10 within it) may be immersed in a basin of heparinized saline for later use, if desired.

Thus it will be appreciated that, by the simple and inexpensive provision of a sheath 50 having features of an embodiment of the present invention, and using a simple and inexpensive series of inventive steps in another embodiment of the invention, a physician user is able to recover the beneficial use of an expensive FFR guidewire 10 that has been tried and failed to reach an opening in a vascular stenosis due to the comparative lack of flexibility that is typically associated with FFR guidewires. These innovations have considerable economic value, because hitherto in the art, FFR guidewires that were determined to be lacking sufficient flexibility to reach a stenosis were discarded and a procedure was adopted that ascertained the need for stent or other intervention using other means such as coronary angiography, intravascular ultrasound, CT coronary angiography, or an FFR catheter.

In another embodiment of the invention and with reference to FIG. 12, a sheath 150 is provided having a modified configuration from that shown in FIG. 4.

Turning to the system of this alternative embodiment of the invention as exemplified in FIG. 12, the sheath 150 of this embodiment is also designed to be extremely simple, comprising few elements and thus being inexpensive to manufacture. The sheath 150 comprises a tube 152 having an internal lumen 151 sized just large enough to receive an FFR guidewire 10 of the kind discussed above. The lumen 151 at the distal end 164 of the tube 152 is blocked or "blind." However, a port 159 for measuring matching aortic pressure is provided on the tube 152, to allow the pressure outside the tube to be measurable locally in the lumen 151 of the tube.

Preferably, the lumen 151 of the tube has an internal diameter between 0.38 and 0.46 mm, and the outer diameter of the tube is between 0.46 and 0.72 mm. In some embodiments, the wall thickness of the tube may be so thin that the tube itself does not have independent column strength to be pushable; however, as will be seen, the tube is configured to receive an FFR guidewire 10, which will impart an overall stiffness to provide sufficient column strength for pushability. The sheath 150 includes a proximal marker 158 adjacent a proximal end of the sheath. The sheath also has a distal marker 156 adjacent a distal end of the tube 52, and also a pullback marker 157 a short distance proximal to the distal marker. The sheath also comprises an Rx portion 154 which is a cylinder of short length, connected to the tube 152 at the distal end of the tube. The Rx portion defines a lumen 153 which is sized just large enough to receive a conventional guidewire 14 of the kind discussed above. Preferably, the lumen of the Rx portion is between 0.38 and 0.46 mm in diameter, and the length of the Rx portion is between 100 and 400 mm. The sheath 150 also comprises a standard hemostasis valve 160 attached to the proximal end of the tube 152, the hemostasis valve optionally including a standard side arm 162.

Figure 13:
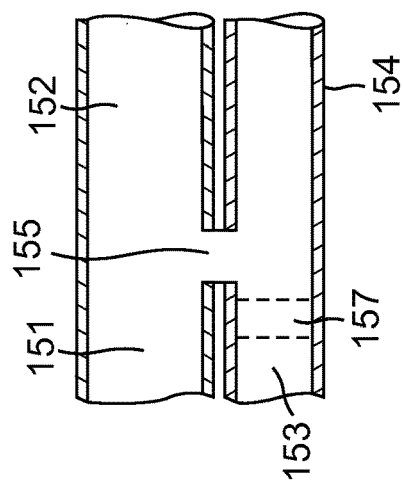
FIG. 13 is a sectional view of a detail of the sheath seen in FIG. 12, at the location marked "A" in FIG. 12.

At or distal to the pullback marker 157 on the sheath 150 a port 155 is defined that places the lumen of the RX portion 154 and the lumen of the tube 152 in fluid communication. FIG. 13.

Turning to another embodiment of the invention, a method is described for using a sheath 150 generally of the kind described above with respect to this embodiment, in order to redeploy an FFR guidewire 10 that has been found to be too inflexible to reach a vascular stenosis, and which has consequently been withdrawn from the patient's vasculature. This method executes steps that include the following and may be envisaged with reference to FIGS. 14-16.

Guide Catheter is Left in the Vasculature; Conventional Guidewire is Inserted: FIG. 7

The guide catheter 104 which was used in the unsuccessful attempt to place the FFR guidewire is left within the patient's vasculature. A conventional guidewire 14 is fed through the guide catheter 104 and is threaded through the vasculature to position its distal tip 18 at a location distal to the target stenosis 102. FIG. 7 shows the result of this step that is common to both method embodiments, and may also be common to a final step in the method embodiments.

Figure 14:
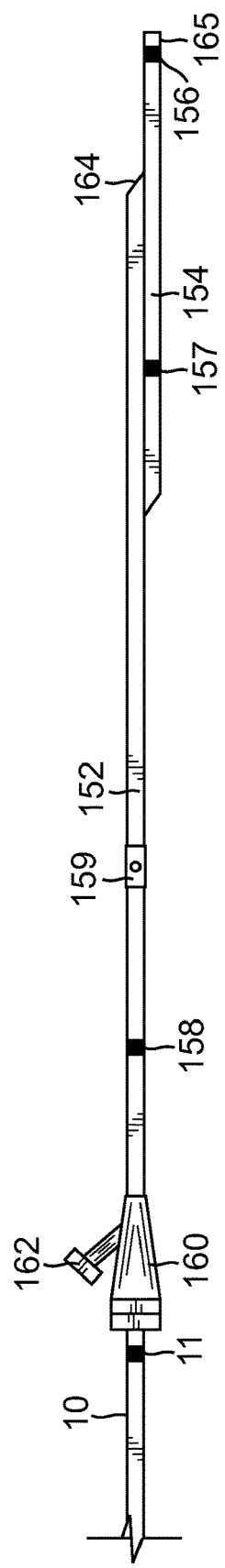
FIG. 14 is a side view of the sheath of FIG. 12, into which a pressure sensing guidewire has been inserted, in the process of carrying out a step of a further embodiment of the invention.

The FFR Guidewire is Inserted into the Sheath: FIG. 14

The FFR guidewire, having been withdrawn from the patient's vasculature, is wetted and flushed.

The sheath 150 is wetted and flushed. Where a side arm 162 is present, the side arm may be used to initially flush the lumen 151 of the tube 152. Where no side arm is present, the lumen 151 of the tube 152 may be flushed by attaching a syringe to the proximal end of the hemostasis valve. The side arm is an optional feature because the guidewire introducer can be easily designed to attach to a syringe and thus, also be used to initially flush this internal lumen of the sheath via the hemostasis valve. To facilitate more complete initial flushing of the lumen 151 of the tube 152, it may be noted that the port 155 (FIG. 13) that communicates between the distal end of the lumen 151 of the tube and the Rx portion lumen 153 may be sized to permit vigorous flushing.

A lubricious coating may be applied to the exterior surface and interior surface of the sheath 150, and to the exterior surface of the FFR guidewire 10. The FFR guidewire 10 is zeroed in a conventional manner.

The hemostasis valve 160 on the proximal end of the sheath 150 is opened. The FFR guidewire 10 is inserted through the valve up to the proximal marker 11 on the FFR guidewire 10 and then close the hemostasis valve 160 to hold and seal the FFR guidewire in place inside the lumen 151 of the tube 152. The position of the proximal marker 11 on the FFR guidewire 10 is located such that the distal end 16 of the FFR guidewire will not contact the distal end of the blind, or blocked, lumen 151 of tube 152, but will be as close to the end of that lumen as practical. FIG. 14. Significant FFR guidewire distal end contact with the distal end of this lumen can produce forces and deformations that may damage the FFR guidewire during sheath 150 positioning. Having the FFR guidewire as fully distal as practical in this lumen 151, provides the sheath 150 with the support necessary for sheath 150 pushability, while allowing the outside diameter of the sheath 150 to be minimized. A minimum outside diameter on the FRR sheath allows smaller guide catheters to be used (less procedure complications), while maintaining the ability of the guide catheter to accurately measure aortic pressure at its proximal end (for systemic blood pressure measurement and FRR/guidewire pressure matching uses).

Figure 15:
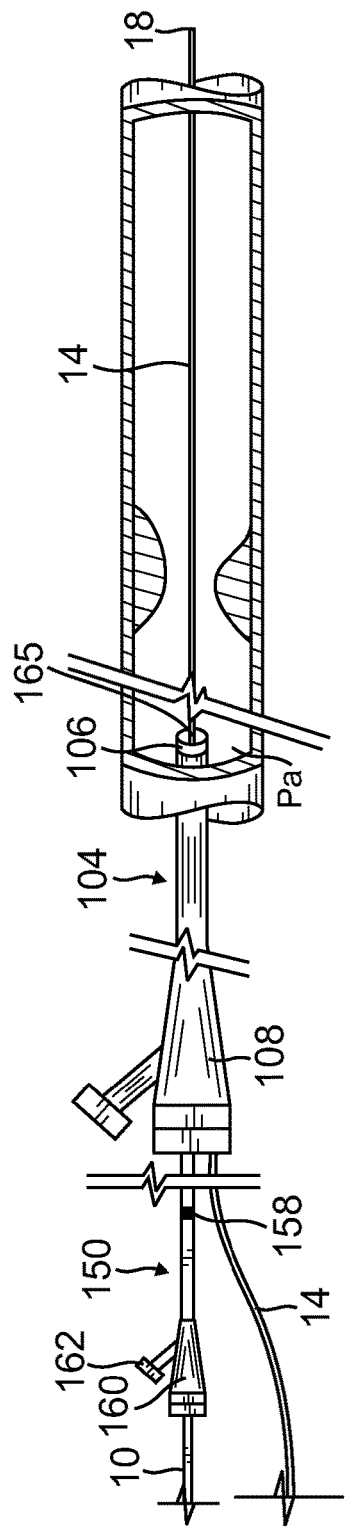
FIG. 15 is a schematic view in partial cutaway of the vessel seen in FIG. 7, showing the state of medical components at a subsequent stage of one of the steps used in an embodiment of the inventive method.

Sheath and FFR Guidewire Advanced to End of Guide Catheter: FIG. 15

The proximal end of the conventional guidewire 14 is engaged with the distal end 164 of the Rx portion lumen 153 of the sheath 150. The hemostasis valve 108 on the proximal end to the guide catheter 104 is opened. The sheath 150 is advanced through the valve 108 over the conventional guidewire 14 up to the proximal marker 150 on the sheath 150 in the conventional manner. The proximal marker 158 on the sheath 150 is positioned such that the distal tip 165 of the sheath 150 will be positioned near the distal end 106 of the guide catheter 104, but not outside of the guide catheter. FIG. 15. Alternatively, the proximal marker 158 may be omitted from the design of the sheath 150 and the insertion of the sheath 150 into the guide catheter observed under fluoroscopy. In this case, the physician may advance the sheath 150 into the guide catheter until he observes the sheath (radiopaque) distal tip marker 156 come adjacent to the distal tip 106 marker of the guide catheter 104.

The hemostasis valve 108 on the proximal end of the guide catheter 104 is closed to hold and seal the sheath 150 and conventional guidewire 14 in position inside the guide catheter.

The hemostasis valve 160 on the proximal end of the sheath 150 is opened, and the FFR guidewire 10 is withdrawn until the distal marker 13 on the FFR guidewire 10 is visible. Then, the hemostasis valve 160 is closed to hold and seal the FFR guidewire in place inside the sheath. In one embodiment, the distal marker 13 on the FFR guidewire 10 may be located such that when it is adjacent valve 160, the pressure sensor 12 is positioned at or near the aortic pressure matching port 159 on the sheath. This port places the lumen 151 of the tube 152 in fluid communication with the blood or fluid in the lumen 105 of the guide catheter 104, of which a fluid column is at aortic blood pressure (systemic blood pressure) Pa. Thus, the pressure sensor 12 in the FFR guidewire is subjected to and may measure the aortic blood pressure Pa. In some embodiments, the diameter of the lumen 151 of the tube 152 in the vicinity of the aortic pressure matching port 159 is increased to assure the pressure sensor 12 is not masked from the aortic blood pressure.

The FFR guidewire's pressure measurement waveform is matched to the aortic pressure (Pa) in the conventional manner.

If it has not already been done, the hemostasis valve 160 on the proximal end of the sheath 150 is opened. The FFR guidewire 10 is advanced up to the proximal marker 11 on the FFR guidewire and then the hemostasis valve 160 is closed to hold and seal the FFR guidewire in place inside the sheath 150. This step ensures the FFR guidewire is placed distally in the sheath and prepares for the next step.

Figure 16:
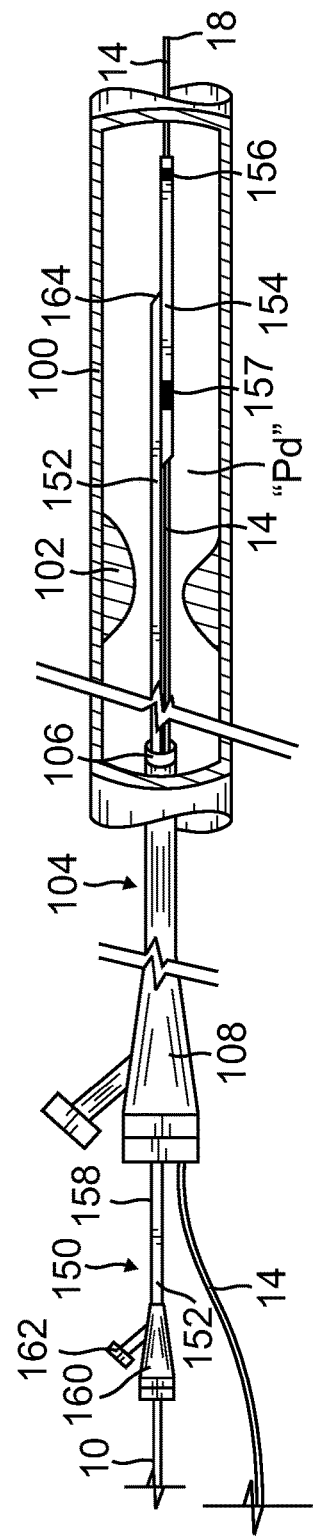
FIG. 16 is a schematic view in partial cutaway of the vessel seen in FIG. 7, showing the state of medical components at a subsequent stage of one of the steps used in an embodiment of the inventive method.

Sheath and FFR Guidewire are Advanced Beyond Stenosis: FIG. 16

The hemostasis valve 108 on the proximal end of the guide catheter 104 is opened and, under fluoroscopy, the sheath 150 is advanced over the conventional guidewire 14 until its radiopaque distal tip marker 156 is distal to the target lesion 102. Under fluoroscopy, the conventional guidewire 14 is withdrawn until its (radiopaque) distal tip 18 is at or just proximal of the (radiopaque) pull back marker 157 on the sheath 150. The hemostasis valve 108 on the proximal end of the guide catheter 104 is closed to hold and seal the sheath 150 and conventional guidewire 14 in position.

At or distal to the pullback marker 157 on the sheath 150 the port 155 (FIG. 13) places the RX portion's lumen 153 and the tube's lumen 151 in fluid communication. With the FFR guidewire 10 in its distal position within its lumen in the sheath 150, the FFR guidewire's pressure sensor 12 is positioned at or near this port 155.

When the conventional guidewire 14 is retracted proximal of this port 155 there is a low flow resistance path between the blood distal to the target lesion (for example, at the point marked Pd and the pressure sensor 12 via the distal portion of the Rx portion lumen 153. Conversely, there is a high flow resistance path between the blood proximal of the target lesion and the pressure sensor 12 via the proximal portion of the Rx portion lumen 153 (proximal of the pull back marker) because that portion of the Rx portion lumen is obstructed by the presence of the distal portion of the conventional guidewire 14. Additionally, there is a high flow resistance path between the blood at the aortic pressure matching port 159 and the pressure sensor 12 because the tube's lumen 151 length is obstructed by the body of the FFR guidewire 10. In some embodiments, the diameter of the tubes' lumen 151 is increased in the vicinity of the port 155 to the Rx portion lumen 153 to assure that the pressure sensor is not shielded from the blood pressure. In consequence of this geometry, the blood in contact with the FFR guidewire's pressure sensor will be at the pressure that is distal to the target lesion (Pd).

In the conventional manner, adenosine is injected into the guide catheter 104 and the measurement of Pd is made.

The hemostasis valve 108 on the proximal end of the guide catheter 104 is opened and, under fluoroscopy, the sheath 150 is held in position relative to the guide catheter 104. The conventional guidewire 14 is moved distally until its distal tip is distal to the target lesion (distal to the distal tip marker 156 of the sheath). This prepares the system for the next step.

Conventional Guidewire Advanced, Sheath and FFR Guidewire Removed: FIG. 7

The conventional guidewire 14 is held in position relative to the guide catheter 104. The sheath 150 (along with the FFR guidewire 10 secured inside it) is withdrawn. The hemostasis valve on the proximal end of the guide catheter is closed to hold and seal the conventional guidewire in position. This leaves the conventional guidewire distal to the target lesion and ready for use by a therapeutic catheter. FIG. 7 shows a common configuration of this condition.

The Sheath 150 (and the FFR guidewire 10 within it) may be immersed in a basin of heparinized saline for later use, if desired.

Thus it will be appreciated that, by the simple and inexpensive provision of a sheath 150 having features of another embodiment of the present invention, using a simple and inexpensive series of inventive steps, a physician user is able to recover the beneficial use of an expensive FFR guidewire 10 that has been tried, yet failed to reach or cross a vascular stenosis due to the lack of flexibility that is typically associated with FFR guidewires. This has considerable economic value because, hitherto in the art, FFR guidewires that were determined to be too inflexible or to have too poor a flexibility profile to reach and pass through a stenosis were discarded, and a procedure was adopted that ascertained the need for stent or other intervention using other means such as coronary angiography, intravascular ultrasound, CT coronary angiography or FFR catheter.

The following comments are made by way of further clarification to various aspects described above with respect to the embodiment of FIG. 14.

Referring back to the step in which the pressure sensor is matching the aortic pressure, the conventional guidewire 14 is filling the entire length of the lumen 153 of the RX portion 154. Thus, there are high flow resistance paths for blood from either end of the Rx portion lumen 153 to the pressure sensor 12 and a low flow resistance path for blood in the guide catheter (at aortic pressure) to the pressure sensor via the aortic pressure matching port. Thus, during this step, the FFR guidewire's pressure sensor 12 is correctly measuring aortic (systemic) blood pressure.

The length of the distal portion of the Rx portion lumen 153 should be 10 cm or longer (at least 15 cm is recommended) to assure that when the distal tip of the sheath 150 is distal to the most distal target lesion, that a the lower outside diameter portions of the Sheath 150 are in the coronary and thus, are only minimally obstructing blood flow during FFR measurements. The length of the proximal portion of the Rx portion lumen 153 must be longer than the longest floppy distal portions of conventional guidewire to avoid guidewire prolapse and thus, may be as long as 25 cm or more.

Although this invention has been disclosed in the context of certain embodiments and examples, it will be understood by those skilled in the art that the invention extends beyond the specifically disclosed embodiments to other alternative embodiments and/or uses of the invention and modifications and equivalents thereof. It is also contemplated that various combinations or sub-combinations of the specific features and aspects of the embodiments may be made and still fall within the scope of the invention. Thus, it is intended that the scope of the invention herein disclosed should not be limited by the particular embodiments described above, but by the claims that are allowed.

I claim:

1. A method for assessing a lesion in a patient's vasculature, comprising:
    inserting into the vasculature of the patient a pressure sensing guidewire that includes a pressure sensor;
    withdrawing the pressure sensing guidewire from the patient's vasculature;
    inserting the pressure sensing guidewire into a proximal end of a tube via a hemostasis valve attached to the tube;
    inserting a conventional guidewire having a proximal end and a distal end into the vasculature of the patient until the distal end of the conventional guidewire is located at a desired location in relation to the lesion;
    inserting the proximal end of the conventional guidewire into a distal end of a lumen of a cylindrical element that is attached to the tube;
    advancing the cylindrical element distally over the conventional guidewire, along with the pressure sensing guidewire inside the tube, through the patient's vasculature until the pressure sensor reaches a desired location with respect to the lesion;
    measuring pressure in the vasculature using the pressure sensor.

* * * * *